United States Patent [19]

Kees

[11] Patent Number: 5,264,451

[45] Date of Patent: Nov. 23, 1993

[54] PROCESS FOR TREATING HYPERGLYCEMIA USING TRIFLUOROMETHYL SUBSTITUTED 3H-PYRAZOL-3-ONES

[75] Inventor: Kenneth L. Kees, Plainsboro, N.J.

[73] Assignee: American Home Products Corporation, New York, N.Y.

[21] Appl. No.: 864,990

[22] Filed: Apr. 7, 1992

[51] Int. Cl.$^5$ ............................................. A61K 31/415
[52] U.S. Cl. ................................... 514/404; 514/407; 514/866; 548/366.1
[58] Field of Search ................ 548/367, 377; 514/404, 514/407, 866

[56] References Cited

U.S. PATENT DOCUMENTS

| | | |
|---|---|---|
| 3,978,077 | 8/1976 | Möller et al. .................. 548/367 |
| 4,099,011 | 7/1978 | Möller et al. .................. 548/367 |
| 4,113,957 | 9/1978 | Moller et al. . | |

FOREIGN PATENT DOCUMENTS

| | | |
|---|---|---|
| 0208874 | 1/1987 | European Pat. Off. . |
| 0449699 | 10/1991 | European Pat. Off. . |
| 55-113706 | 9/1980 | Japan . |
| 55-157504 | 10/1980 | Japan . |

Primary Examiner—Robert W. Ramsuer
Attorney, Agent, or Firm—Richard K. Jackson

[57] ABSTRACT

The compound of the formula:

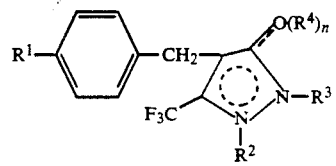

in which the dotted lines represent two sites of unsaturation appropriately located based on the identity of $R^2$, $R^3$ and $R^4$ and, $R^1$ is alkyl, perfluoroalkyl, alkoxy, perfluoroalkoxy, alkylthio, perfluoroalkylthio, alkylsulfinyl, alkylamino, halo, alkanoyl, 1-hydroxyalkyl or (1-hydroxyimino) alkyl; $R^2$ is hydrogen or alkyl; $R^3$ is hydrogen or alkyl; $R^4$ is hydrogen or alkyl; n is 0 or 1; or a pharmaceutically acceptable salt thereof, are antihyperglycemic agents.

1 Claim, No Drawings

PROCESS FOR TREATING HYPERGLYCEMIA USING TRIFLUOROMETHYL SUBSTITUTED 3H-PYRAZOL-3-ONES

BACKGROUND OF THE INVENTION

Japanese patent 55/157504 discloses a group of herbicidal compounds of the formula:

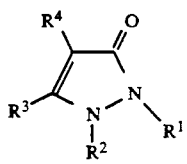

in which $R^1$ is hydrogen or alkyl; $R^2$ is alkyl, alkoxycarbonylmethyl or phenyl; $R^3$ is alkyl; and $R^4$ is hydrogen, alkanoyl, or a substituted or unsubstituted benzyl or benzoyl group.

Japanese patent 55/113706 discloses a group of herbicidal compounds of the formula:

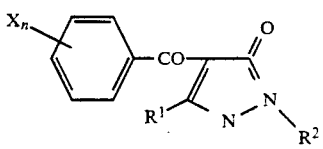

in which $R^1$ and $R^2$ are alkyl, formyl, haloalkyl, hydroxyalkyl, phenyl or halophenyl; X is alkyl, alkoxy, nitro or halo and n is 0-2.

U.S. Pat. No. 4,113,957 discloses 1-substituted-5-acryloxypyrazoles of the formula:

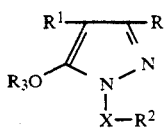

in which R is H, —CF$_3$, alkyl, aryl, heteroaryl or aralkyl; $R^1$ is H, alkyl, aryl or aralkyl; X is alkylene or alkylene-O- or alkylene-S-; $R^2$ is aryl, CF$_3$, alkyl, alkenyl, alkoxy, alkylamino, —CN, OCF, —NO$_2$, —CONH$_2$, —SO$_2$NH$_2$ or —SO$_n$ alkyl. Other variables also apply to the structural formula. These compounds are disclosed to be diuretics, saluretics, antithrombotics and antihypertensives.

EP Application 208,874 discloses a group of compounds of the formula:

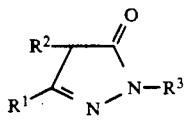

in which $R^1$ is H, aryl, alkyl, or alkoxycarbonylalkyl; $R^2$ is hydrogen, aryloxy, arylmercapto, alkyl or hydroxyalkyl; $R^1$ and $R^2$ together may be alkylene; $R^3$ is hydrogen, alkyl, cycloalkyl, hydroxyalkyl, benzyl, naphthyl or phenyl, substituted or unsubstituted.

BRIEF DESCRIPTION OF THE INVENTION

This invention provides a group of 4-(substituted benzyl)-5-trifluoromethyl-3H-pyrazol-3-ones, the tautomeric forms of the pyrazolones and their O- and N-substituted derivatives. The compounds of this invention present pyrazol-3-one and 3-oxypyrazole structures. They are potent, orally active antihyperglycemic agents useful in the treatment of non-insulin dependent diabetes mellitus.

DETAILED DESCRIPTION OF THE INVENTION

In accordance with the invention, there is provided a group of compounds of the formula:

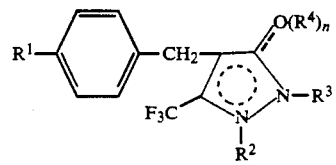

in which the dotted lines represent two sites of unsaturation approximately located based on the identity of $R^2$, $R^3$ and $R^4$ and, $R^1$ is alkyl of 1 to 6 carbon atoms, perfluoroalkyl of 1 to 6 carbon atoms, alkoxy of 1 to 6 carbon atoms, perfluoroalkoxy of 1 to 6 carbon atoms, alkythio of 1 to 6 carbon atoms, perfluoroalkylthio of 1 to 6 carbon atoms, alkylsulfinyl of 1 to 6 carbon atoms, alkylamino of 1 to 6 carbon atoms, halo, alkanoyl of 2 to 6 carbon atoms, 1-hydroxyalkyl of 1 to 6 carbon atoms or 1-(hydroxyimino) alkyl of 1 to 6 carbon atoms;

$R^2$ is hydrogen or alkyl of 1 to 3 carbon atoms;
$R^3$ is hydrogen or alkyl of 1 to 3 carbon atoms;
$R^4$ is hydrogen or alkyl of 1 to 3 carbon atoms;
n is 0 or 1;
or a pharmaceutically acceptable salt thereof.

The preferred compounds are those best depicted by the formula:

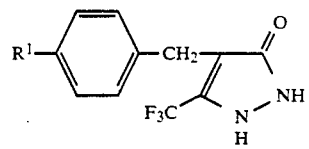

in which
$R^1$ is alkyl of 1 to 3 carbon atoms, alkylthio of 1 to 3 carbon atoms or alkylsulfinyl of 1 to 3 carbon atoms;

or a pharmaceutically acceptable salt thereof and those best depicted by the formula:

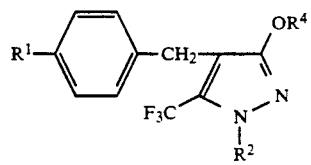

in which
$R^1$ is alkylthio of 1 to 3 carbon atoms;
$R^2$ is alkyl of 1 to 3 carbon atoms; and
$R^4$ is alkyl of 1 to 3 carbon atoms;

or a pharmaceutically acceptable salt thereof and those best depicted by the formula:

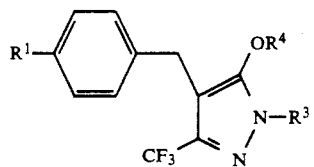

in which
R$^1$ is alkylthio of 1 to 3 carbon atoms;
R$^3$ is alkyl of 1 to 3 carbon atoms; and
1 R$^4$ is alkyl of 1 to 3 carbon atoms;
or a pharmaceutically acceptable salt thereof.

In the compounds disclosed above, the alkyl group representing R$^{1-4}$ are methyl, ethyl, propyl, isopropyl, butyl, tert-butyl, pentyl, hexyl, and the like, the methyl, ethyl, propyl and isopropyl groups being preferred; the perfluoroalkyl groups are trifluoromethyl, pentafluoroethyl or heptafluoropropyl; the alkoxy groups correspond in size to the alkyl groups defined above; and the halogens are chloro, bromo, fluoro and iodo, the first two being preferred.

The pharmaceutically acceptable salts of the compounds of this invention where R$^1$ is alkylamino may be derived from known inorganic and organic acids such as hydrochloric, oxalic, tartaric, fumaric, lactic, phosphoric, p-toluene sulfonic, formic, hydrobromic, maleic, sulfamic acids, and the like. Salts of the pyrazole group with bases are readily formed. Suitable cations are the alkali metals (Na or K) the alkaline earth metals (Mg or Ca), ammonium or primary or secondary alkyl amines.

The compounds of this invention are prepared conventionally by the reaction of:

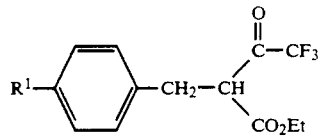

with hydrazine.

The following examples illustrate the preparation of representative compounds of this invention. The compounds are named as 3H-pyrazol-3-one derivatives and as alkoxy 1H-pyrazole derivatives, although it is recognized that they may occur in other tautomeric forms, such as in the following generalized structures:

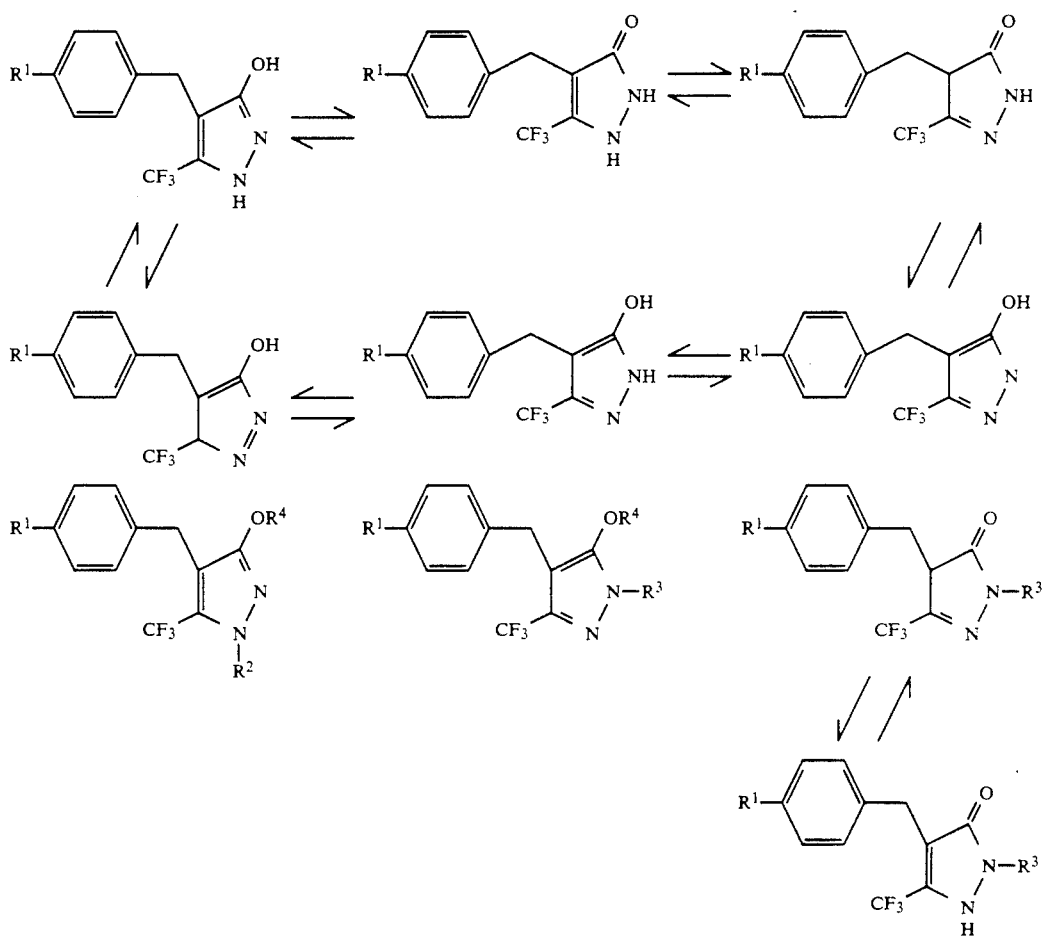

EXAMPLE 1

1,2-Dihydro-4-[(4-methylthiophenyl)methyl]-5-(trifluoromethyl)-3H-pyrazole-3-one A solution of 4-methylthiobenzyl alcohol (20 g) and carbon tetrabromide (47.4 g) in dichloromethane (450 mL) was cooled to 0° C. under N$_2$ atmosphere. Triphenyl phosphine (37.4 g) was added portionwise over 0.5 hours and the resulting mixture allowed to warm gradually to ambient temperature. The reaction mixture was poured onto saturated aqueous NaCl solution. The organic phase was dried over MgSO$_4$, concentrated in vacuo on the rotary evaporator and filtered through a silica gel column with the aid of dichloromethane. Volatile materials were removed on the rotary evaporator and the residue was triturated with hot heptane. The heptane solution was allowed to stand at room temperature overnight, filtered and concentrated. This process was repeated twice with petroleum ether to give a quantitative yield of 4-(methylthiophenyl)methyl bromide as a yellow mobile oil.

Sodium hydride (2.76 g, 60% oil dispersion) in 1,2-dimethoxyethane (50 mL) was cooled to 0° C. with stirring under N$_2$ atmosphere. Ethyl 4,4,4-trifluoromethyl acetoacetate (12.7 g) was added dropwise at a rate so as to control H$_2$ evolution. When the addition was complete the homogeneous solution was warmed to reflux temperature and a solution of 4-(methylthiophenyl)methyl bromide (15 g) in 1,2-dimethoxyethane (100 mL) was added. The reaction mixture was refluxed 15 hours, cooled to room temperature, and volatile materials were removed in vacuo on the rotary evaporator. The residue was partitioned between 1N aqueous HCl solution and ethyl acetate. The organic phase was washed with additional 1N HCl solution (2×50 mL) and with saturated aqueous NaCl solution, dried over MgSO$_4$ and concentrated. The residue was kugelrohr distilled at reduced pressure (~0.5 mm Hg). Excess starting β-keto ester was collected below 100° C. oven temperature and the desired ethyl-α-(trifluoroacetyl)-3-(4-methylthiophenyl) propionate (12.2 g) was collected at 115°-140° C. oven temperature.

A mixture of ethyl α-(trifluoroacetyl)-3-(4-methylthiophenyl) propionate (6 g), anhydrous hydrazine (0.92 mL) and toluene were refluxed 15 hours. The reaction mixture was cooled to ambient temperature and concentrated to a tan solid. The residue was triturated with hot toluene (steam bath). The solution was decanted and the product crystallized on standing. The title compound, as white crystals, weighed 1.08 g after 15 hours in an abderdalden apparatus (ethanol, reflux), mp 147.5°-148.5° C.

Elemental analysis for: C$_{12}$H$_{11}$F$_3$N$_2$OS: Calc'd: C, 50; H, 3.85; N, 9.72. Found: C, 50.27; H, 3.77; N, 9.41.

EXAMPLE 2

1,2-Dihydro-4-[(4-ethylthiophenyl)methyl]-5-(trifluoromethyl)-3H-pyrazol-3-one

The title compound, prepared as in Example 1, when recrystallized from hexane-toluene mixture gave a tan solid which was recrystallized from toluene to give white needles, mp 133°-134° C.

Elemental analysis for: C$_{13}$H$_{13}$F$_3$N$_2$OS: Calc'd: C, 51.65; H, 4.33; N, 9.27. Found: C, 51.83; H, 4.37; N, 9.21. The starting 4-(ethylthio)benzyl alcohol was prepared as follows. A mixture of lithium aluminum hydride (5.2 g) and tetrahydrofuran (250 mL) was cooled to 0° C. with stirring under N$_2$ atmosphere. A solution of 4-(ethylthio)benzoic acid (25 g) in tetrahydrofuran (300 mL) was added at a rate so as to control H$_2$ evolution. The reaction mixture was then allowed to warm to room temperature and stirred 15 hours. The mixture was cooled in ice and a solution of 15% aqueous sodium hydroxide solution was added, (6 mL) followed by water (21 mL). The mixture was stirred at ice temperature for 1 hour and for 2 hours at ambient temperature. The solution was decanted, diluted with diethyl ether and washed with saturated aqueous NaCl solution. The organic phase was dried over MgSO$_4$, filtered through a celite pad and concentrated to give 4-(ethylthio)benzyl alcohol (20 g). This material was converted to the corresponding bromide as in Example 1 except that diethyl ether and hexane were used for the triturations rather than heptane and petroleum ether, respectively.

EXAMPLE 3

1,2-Dihydro-4-[4-(isopropylthiophenyl)methyl]-5-(trifluoromethyl)-3H-pyrazol-3-one The title compound was prepared as in Example 1. The crude product was recrystallized from benzene to give white needles, mp 169°-170° C.

Elemental analysis for: C$_{14}$H$_{15}$F$_3$N$_2$OS: Calc'd: C, 53.16; H, 4.78; N, 8.86. Found: C, 53.31; H, 4.81; N, 8.64.

The starting 4-(isopropylthio)benzyl alcohol was prepared as follows. To a −78° C. solution of 4-bromobenzyl alcohol (25 g) in tetrahydrofuran (350 mL) and tetramethylethylenediamine (42.5 mL) under N$_2$ atmosphere was added a solution of n-butyllithium in hexane (202 mL, 1.6M). The reaction mixture was held at −78° C. for 1.5 hours, warmed to 0° C. for 0.5 hours, then re-cooled to −78° C. and a solution of diisopropyldisulfide (20 g) in tetrahydrofuran (300 mL) added dropwise. The mixture was allowed to warm to room temperature gradually and stirred 15 hours. The reaction mixture was cooled in ice, quenched with aqueous 1N HCl solution and extracted with ethyl acetate. The extracts were washed with additional HCl solution followed by saturated aqueous NaCl solution and dried over MgSO$_4$. The extracts were concentrated on a rotary evaporator and the crude amber oil was partially purified by distillation on a kugelrohr apparatus (undesired material collected at oven temperature 23°-65° C.). The pot residue contained 20.5 g of 4-isopropylbenzyl alcohol which was used as in Example 1 without further purification.

EXAMPLE 4

1,2-Dihydro-4-[4-(methylsulfinylphenyl)methyl]-5-(trifluoromethyl)-3H-pyrazol-3-one The title compound from Example 1 (2.5 g) in acetone (40 mL) was treated with aqueous hydrogen peroxide solution (1 mL, 30%) at room temperature for 24 hours. The precipitate was collected on a Buchner funnel, washed with H$_2$O and with diethyl ether and dried under vacuum to give about 1 g of white solid, mp 200.5°-201.5° C.

Elemental analysis for: C$_{12}$H$_{11}$F$_3$N$_2$O$_2$S$_2$: Calc'd: C, 47.37; H, 3.64; N, 9.21. Found: C, 47.30; H, 3.64; N, 9.17.

EXAMPLE 5

1,2-Dihydro-4-[4-(methoxyphenyl)methyl]-5-(trifluoromethyl)-3H-pyrazol-3-one

The title compound was prepared as in Example 1 starting from 4-methoxybenzyl chloride. The crude product was recrystallized from hot toluene-hexane mixture to give white crystals, mp 181°-183° C.

Elemental analysis for: C$_{12}$H$_{11}$F$_3$N$_2$O$_2$: Calc'd: C, 52.95; H, 4.07; N, 10.29. Found: C, 53.09; H, 4.33; N, 10.21.

EXAMPLE 6

1,2-Dihydro-4-[4-(trifluoromethoxyphenyl)methyl]-5-(trifluoromethyl)-3H-pyrazol-3-one The title compound was prepared as in Example 1 and was recrystallized twice from toluene-hexane mixture and vacuum dried (abderhalden apparatus) to give yellow crystals, mp 90°–91° C.

Elemental analysis for: $C_{12}H_8F_6N_2O_2$: Calc'd: C, 44.19; H, 2.47; N, 8.59. Found: C, 44.00; H, 2.60; N, 8.52.

The starting 4-(trifluoromethoxyphenyl)methyl bromide was prepared as follows. To a cold (−78° C.) solution of 4-(trifluoromethoxy)benzyl alcohol (15 g, prepared as in Example 2 from the reduction of the corresponding acid by lithium aluminum hydride) in dichloromethane (375 mL) under $N_2$ atmosphere was added boron tribromide (4.9 mL). The reaction was stirred at −78° C. for 1 hour, then allowed to warm to ambient temperature, and stirred 6 hours. The mixture was cooled to −20° C., anhydrous methanol (150 mL) was added and the mixture stirred 15 hours at room temperature. Volatile materials were removed in vacuo on the rotary evaporator (80° C. bath) and the residue treated with 2×150 mL portions of methanol (stirring about 2 hours each) followed by concentration. The product was dissolved in warm hexane, filtered through a short florisil pad with the aid of hexane and concentrated on the rotary evaporator. The 4-(trifluoromethoxyphenyl)methyl bromide so obtained was homogeneous by TLC ($CH_2Cl_2$) and was used without further purification as in Example 1.

EXAMPLE 7

1,2-Dihydro-4-[4-(trifluoromethylthiophenyl)methyl]5-(trifluoromethyl)-3H-pyrazol-3-one The title compound was prepared as in Example 1. The crude product was purified by reverse phase chromatography (silica gel) using a methanol-$H_2O$ elution gradient (10:90→60:40) in order to separate the title compound from the 4-(4-chlorophenylmethyl) analogue (see Example 10). The title compound was obtained as a white powder, mp 125°–127° C.

Elemental analysis for: $C_{12}H_8F_6N_2OS$: Calc'd: C, 42.11; H, 2.36; N, 8.18. Found: C, 42.34; H, 2.62; N, 8.15.

The starting 4-(trifluoromethylthio)phenylmethyl bromide was prepared as follows. Under $N_2$ atmosphere a mixture of magnesium turnings (9.6 g) aluminum triisopropoxide (catalytic amount), and a few grams of 4-chlorotoluene in tetrahydrofuran (75 mL) were warmed with a heat gun until Grignard formation was initiated. A solution of 4-chlorotoluene (50 g) in THF (200 mL) was added at a rate so as to maintain reflux without external heating. When addition was complete the reaction was maintained at reflux for 15 hours. The reaction mixture was cooled in ice and trifluoromethylsulfenylchloride was bubbled through the mixture for 1.5 hours. The reaction mixture was allowed to warm to ambient temperature gradually and stirred for 15 hours. The mixture was cooled in ice and a solution of sulfuric acid (2.5N, 500 mL) was added portionwise over 0.3 hours. The mixture was extracted with petroleum ether (30°–60° C.) and the extracts were washed with saturated aqueous NaCl solution and dried over $MgSO_4$. Distillation at reduced pressure provided 23.8 g of 4-(trifluoromethylthio) toluene (collected at still head temperature 98°–105° C./90 mmHg) contaminated with starting 4-chlorotoluene. The mixture (about 2:1) was used directly in the next step without further purification.

The above mixture of 4-(trifluoromethylthio)toluene (about 3.6 g) and 4-chlorotoluene (about 1.8 g) N-bromo succinimide (6.8 g), carbon tetrachloride (35 mL) and azo(bis)isobutylnitrile (AIBN, catalytic amount) were refluxed 15 hours. Additional N-bromo succinimide (about 1 g) and AIBN were added and reflux was continued another 24 hours. The reaction mixture was cooled to room temperature, filtered and concentrated in vacuo on the rotary evaporator to give a mixture of bromides which were used as in Example 1 without further purification.

EXAMPLE 8

1,2-Dihydro-4-[(4-ethylaminophenyl)methyl]-5-(trifluoromethyl)-3H-pyrazol-3-one

A solution of borane-THF complex (188 mL, 1M solution in tetrahydrofuran), diluted with 200 mL tetrahydrofuran, was cooled to −30° C. under $N_2$ atmosphere. A solution of 4-[(4-acetamidophenyl)methyl]-5-(trifluoromethyl)-3H-pyrazol-3-one (6 g, prepared as in Example 1 (except that 4-acetamidobenzylchloride was reacted with the β-keto ester anion in refluxing xylene) in tetrahydrofuran (300 mL) was added over 0.75 hours and the mixture allowed to warm gradually to ambient temperature with stirring for 15 hours. The reaction mixture was refluxed for 3 hours, then cooled in ice and quenched with aqueous sodium hydroxide solution (24 mL, 2.5N). The mixture was stirred for 2 hours at ice temperature and 15 hours at room temperature. Volatile materials were removed in vacuo on the rotary evaporator. The residue was solubilized in distilled water, brought to pH 7 with dilute, aqueous HCl solution and extracted with ethyl acetate. The extracts were washed with saturated brine solution, dried over $MgSO_4$, filtered and concentrated. The residue was dissolved in isopropyl alcohol saturated with anhydrous HCl and cooled in ice. The precipitate was collected on a suction funnel and dried under vacuum (abderhalden apparatus) to afford the title compound as a pale yellow glass; sinters at 104° C., liquefies 169°–171° C.

Elemental analysis for: $C_{13}H_{14}F_3N_3O.HCl.0.75-H_2O.0.5C_3H_8O$ (isopropanol): Calc'd: C, 46.89; H, 5.07; N, 12.4. Found: C, 46.89; H, 5.35; N, 12.03.

EXAMPLE 9

1,2-Dihydro-4-[(4-fluorophenyl)methyl]-5-(trifluoromethyl)-3H-pyrazol-3-one

The title compound was prepared as in Example 1. HPLC purification provided the title compound as a yellow oil which crystallized upon trituration with petroleum ether, mp 159°–160° C.

Elemental analysis for: $C_{11}H_8F_4N_2O$: Calc'd: C, 50.78; H, 3.10; N, 10.77. Found: C, 50.73; H, 2.93; N, 10.6.

EXAMPLE 10

4-[(4-Chlorophenyl)methyl]-1,2-dihydro-5-(trifluoromethyl)-3H-pyrazol-3-one

The title compound was prepared as in Example 1 except that 4-(chlorophenyl)methyl chloride was reacted with the β-keto ester anion in refluxing toluene with 1.1 equivalents LiBr added. The title compound was purified by recrystallization from toluene to afford white crystals, mp 151°–152° C.

Elemental analysis for: $C_{11}H_8ClF_3N_2O$: Calc'd: C 47.76; H, 2.91; N, 10.13. Found: C, 47.74; H, 2.88; N, 10.01.

EXAMPLE 11

4-[(4-Bromophenyl)methyl]-1,2-dihydro-5-(trifluoromethyl)-3H-pyrazol-3-one

The title compound was prepared as in Example 1. The crude product was recrystallized from diethyl ether-hexane mixture to afford the title compound as a white solid, mp 135°–136.5° C.

Elemental analysis for: $C_{11}H_8BrF_3N_2O$: Calc'd: C, 41.5; H, 2.51; N, 8.72. Found: C, 41.22; H, 2.41; N, 8.85.

EXAMPLE 12

1,2-Dihydro-4-[(4-iodophenyl)methyl]-5-(trifluoromethyl)-3H-pyrazol-3-one

The title compound was prepared as in Example 1 except that the reaction with hydrazine was started at −50° C. (held for 1 hour) then warmed to reflux temperature. (The starting bromide was prepared as in Example 6). The crude product crystallized from hot heptane, mp 133°–134° C.

Elemental analysis for: $C_{11}H_8F_3IN_2O$: Calc'd: C, 35.89; H, 2.19; N, 7.61. Found: C, 35.95; H, 2.10; N, 7.27.

EXAMPLE 13

1,2-Dihydro-4-[(4-methylphenyl)methyl]-5-(trifluoromethyl)-3H-pyrazol-3-one

The title compound was prepared as in Example 1. Two recrystallizations from diethyl ether-hexane gave the title compound as yellow crystals, mp 150°–151.5° C.

Elemental analysis for: $C_{12}H_{11}F_3N_2O$: Calc'd: C, 56.26; H, 4.33; N, 10.93. Found: C, 55.97; H, 4.07; N, 10.91.

EXAMPLE 14

1,2-Dihydro-4-[(4-ethylphenyl)methyl]-5-(trifluoromethyl)-3H-pyrazol-3-one

The title compound was prepared as in Example 1 except that anhydrous 1,2-dimethoxyethane was used as solvent in the reaction with hydrazine. Recrystallization from hot hexane-diethyl ether mixture provided the title compound as a yellow powder, mp 128°–130° C.

Elemental analysis for: $C_{13}H_{13}F_3N_2O$: Calc'd: C, 57.78; H, 4.85; N, 10.37. Found: C, 57.69; H, 4.60; N, 10.39.

EXAMPLE 15

1,2-Dihydro-4-[(4-propylphenyl)methyl]-5-(trifluoromethyl)-3H-pyrazol-3-one

The title compound was prepared as in Examples 1 and 2. Recrystallization from cold hexane-diethyl ether mixture provided the title compound as a tan powder, mp 114°–116° C.

Elemental analysis for: $C_{14}H_{15}F_3N_2O \cdot 0.25H_2O$: Calc'd: C, 58.20; H, 5.37; N, 9.70. Found: C, 58.39; H, 5.34; N, 10.01.

EXAMPLE 16

1,2-Dihydro-4-[(4-isopropylphenyl)methyl]-5-(trifluoromethyl)-3H-pyrazol-3-one

The title compound was prepared as in Example 1 except that 1,2-dimethoxyethane was used as solvent in the reaction with hydrazine. (The starting 4-isopropylbenzyl alcohol was obtained from reduction of 4-isopropylbenzaldehyde with lithium aluminum hydride as in Example 2). The crude product was recrystallized twice from hexane-diethyl ether mixture to afford the title compound as a white solid, mp 139°–141° C.

Elemental analysis for: $C_{14}H_{15}F_3N_2O$: Calc'd: C, 59.15; H, 5.32; N, 9.85. Found: C, 59.55; H, 5.32; N, 9.91.

EXAMPLE 17

1,2-Dihydro-4-[(4-trifluoromethylphenyl)methyl]-5-(trifluoromethyl)-3H-pyrazol-3-one The title compound was prepared as in Example 1 except that 1,2-dimethoxyethane was used as solvent in the hydrazine reaction. The crude product was recrystallized from hexane-diethyl ether mixture and from toluene-hexane mixture to give the title compound as white crystals, mp 123°–124.5° C.

Elemental analysis for: $C_{12}H_8F_6N_2O$: Calc'd: C, 46.46; H, 2.60; N, 9.03. Found: C, 46.67; H, 2.64; N, 9.15.

EXAMPLE 18

4-[(4-Acetylphenyl)methyl]-1,2-dihydro-5-(trifluoromethyl)-3H-pyrazol-3-one

The title compound was prepared as in Examples 1 and 7 (except that 1,2-dimethoxyethane was used as solvent in the reaction with hydrazine) from the 1,3-dioxolane derivative of the 4-acetyl group. The reaction mixture from the pyrazolone forming reaction was treated with concentrated HCl at room temperature to effect hydrolysis of the ethylene ketal protecting group. The mixture was extracted with ethyl acetate and the extracts washed with saturated aqueous NaCl solution, dried over MgSO$_4$ and concentrated. The product was triturated with hexane to give the title compound as white crystals, mp 218.5°–219.5° C.

Elemental analysis for: $C_{12}H_9F_3N_2O_2$: Calc'd: C, 54.93; H, 3.90; N, 9.86. Found: C, 54.7; H, 4.28; N, 9.59.

EXAMPLE 19

1,2-Dihydro-4-[4-[(1-hydroxyethyl)phenyl]methyl]-5-(trifluoromethyl)-3H-pyrazol-3-one The title compound from Example 18 (0.54 g) in THF (70 mL) was cooled in ice under N$_2$ atmosphere. A solution of sodium borohydride (0.81 g) in water (35 mL) was added over 0.5 hours, and the mixture allowed to warm to ambient temperature with stirring 15 hours. The reaction mixture was warmed to reflux temperature for 2 hours, cooled in ice and quenched by dropwise addition of 5N aqueous HCl solution. Volatile materials were removed on the rotary evaporator and the residue was partitioned between ethyl acetate and saturated aqueous brine solution. The organic phase was dried (MgSO$_4$) and concentrated to an amber syrup which produced the title compound as white crystals upon trituration with dichloromethane, mp 154°–155° C.

Elemental analysis for: $C_{13}H_{13}F_3N_2O_2$: Calc'd: C, 54.55; H, 4.58; N, 9.79. Found: C, 54.61; H, 4.47; N, 9.73.

EXAMPLE 20

1,2-Dihydro-4-[4-[(1-hydroxyiminoethyl)phenyl]methyl]-5-(trifluoromethyl)-3H-pyrazol-3-one The title compound from Example 18 (0.53 g), hydroxylamine hydrochloride (0.15 g) and pyridine (60 mL) were stirred at room temperature for 24 hours. Additional hydroxylamine hydrochloride (0.15 g) was added and the mixture heated to 50° C. for 15 hours. Pyridine was removed at reduced pressure and the residue partitioned between ethyl acetate and 5N HCl. The organic phase was washed with saturated brine solution, dried over MgSO$_4$ and concentrated. The oily residue produced the title compound, as pale yellow crystals upon trituration with CH$_2$Cl$_2$, mp 194°–196° C.

Elemental analysis for: C$_{13}$H$_{12}$F$_3$N$_3$O$_2$: Calc'd: C, 52.18; H, 4.04; N, 14.04. Found: C, 52.14; H, 4.42; N, 13.67.

EXAMPLE 21

1,2-Dihydro-5-(trifluoromethyl)-1-methyl-4-[4-(methylthio)phenyl]-3H-pyrazol-3-one A mixture of the title compound from Example 1 (2.5 g), tetramethylethylenediamine (1.44 mL, freshly distilled from calcium hydride), and tetrahydrofuran (30 mL) was cooled to −78° C. under N$_2$ atmosphere. A solution of n-butyllithium (9.1 mL, 2M) in pentane was added dropwise to the vigorously stirred reaction mixture. The mixture was held at −78° C. for 0.3 hours, warmed to ice temperature for 0.25 hours, cooled to −78° C. and methyl iodide (0.8 mL) added dropwise. The reaction was allowed to warm to ambient temperature, stirred 15 hours, cooled in ice and quenched with 1N aqueous HCl solution. The mixture was extracted with ethyl acetate and the extracts washed with saturated brine solution, dried over MgSO$_4$ and concentrated. The residue (a thick black oil) was dissolved in a minimum amount of warm ethyl acetate and left to stand at room temperature for 13 days. The title compound, as pale violet crystals, were collected, washed with diethyl ether and air dried. mp 141.5°–145.5° C.

Elemental analysis for: C$_{13}$H$_{13}$F$_3$N$_2$OS: Calc'd: C, 51.65; H, 4.33; N, 9.27. Found: C, 51.36; H, 4.17; N, 9.16.

EXAMPLE 22

3-Methoxy-4-[4-(methylthiophenyl)methyl]-5-(trifluoromethyl)-1H-pyrazole

A mixture of the title compound from Example 1 (2 g), anhydrous potassium carbonate (1.44 g, pulverized) and acetonitrile (25 mL) refluxed for 1 hour, cooled to room temperature and methyl iodide added to the stirred mixture in portions (4×0.44 mL) over 2 days. The reaction was diluted with enough water to dissolve all salts and the mixture partitioned between ethyl acetate and saturated brine solution. The extracts were washed with saturated brine, dried over MgSO$_4$, concentrated and the residue chromatographed on silica gel (35 wt. eq.). Elution with 10% ethyl acetate/hexane provided the title compound as a white solid, mp 115°–117° C.

Elemental analysis for: C$_{13}$H$_{13}$F$_3$N$_2$OS: Calc'd: C, 51.65; H, 4.33; N, 9.27. Found: C, 51.97; H, 4.28; N, 8.95.

EXAMPLE 23

3-Methoxy-1-methyl-4-[4-(methylthiophenyl)methyl]-5-(trifluoromethyl)pyrazole

The title compound was prepared as in Example 22 except that the reaction was carried out at reflux for 3 days with 5 portions of methyl iodide periodically added to the reaction mixture. Chromatography on silica gel, elution with hexane provided the title compound as a waxy white solid, mp 31°–34° C.

Elemental analysis for: C$_{14}$H$_{15}$F$_3$N$_2$OS: Calc'd: C, 53.16; H, 4.78; N, 8.86. Found: C, 53.05; H, 4.78; N, 8.89.

EXAMPLE 24

4-[4-(Ethylphenyl)methyl]-3-(methoxy)-5-(trifluoromethyl)-1H-pyrazole

The title compound was prepared as in Example 22 starting from the title compound of Example 14. Chromatography on silica gel, elution with 5% ethyl acetate/hexane provided the title compound as a yellow oil.

Elemental analysis for: C$_{14}$H$_{15}$F$_3$N$_2$O.0.75H$_2$O: Calc'd: C, 60.4; H, 5.74; N, 9.39. Found: C, 60.1; H, 5.74; N, 9.13.

EXAMPLE 25

4-[4-(Ethylphenyl)methyl]-3-(methoxy)-1-(methyl)-5-(trifluoromethyl)-pyrazole

The title compound was prepared as in Example 23 from the title compound of Example 14. Chromatography on silica gel, elution with 5% ethyl acetate/hexane provided the title compound as a yellow oil.

Elemental analysis for: C$_{15}$H$_{17}$N$_2$F$_3$O: Calc'd: C, 60.4; H, 5.74; N, 9.39. Found: C, 60.1; H, 5.74; N, 9.13.

EXAMPLE 26

3-Ethoxy-1-(ethyl)-4-[4-(methylthiophenyl)methyl]-5-(trifluoromethyl)pyrazole

The title compound was prepared as in Example 23 from the title compound of Example 1 and ethyl iodide. Chromatography on silica gel, elution with 10% ethyl acetate/hexane provided the title compound as a colorless oil (least polar isomer).

Elemental analysis for: C$_{16}$H$_{19}$F$_3$N$_2$OS: Calc'd: C, 55.8; H, 5.56; N, 8.13. Found: C, 55.92; H, 5.37; N, 8.07.

EXAMPLE 27

5-Ethoxy-1-(ethyl)-4-[4-(methylthiophenyl)methyl]-3-(trifluoromethyl)pyrazole

The title compound was prepared in the same reaction as Example 26. The title compound was the more polar isomer eluted from silica gel, as a yellow oil.

Elemental analysis for: C$_{16}$H$_{19}$F$_3$N$_2$OS: Calc'd: C, 55.8; H, 5.56; N, 813. Found: C, 55.87; H, 5.61; N, 8.14.

Note: the structural assignments for the isomers—Examples 26 and 27 were made on the basis of $^{13}$C-NMR as indicated.

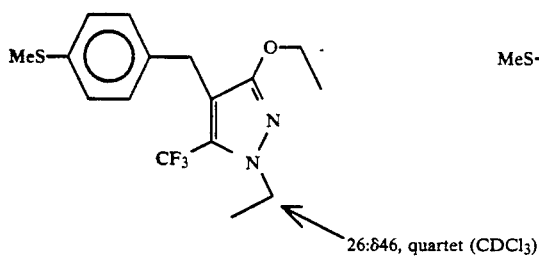

26:δ46, quartet (CDCl₃)

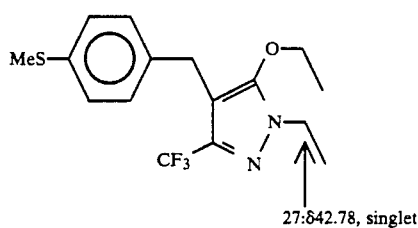

27:δ42.78, singlet

EXAMPLE 28

1-Methyl-4-[(4-methylthiophenyl)methyl]-3-(trifluoromethyl)-2H-pyrazol-5-one

The title compound was prepared as in Example 1 except that methylhydrazine was used instead of hydrazine. Recrystallization from toluene-hexane mixture provided the title compound as off-white crystals, mp 138°–139° C.

Elemental analysis for: $C_{13}H_{13}F_3N_2OS$: Calc'd: C, 51.65; H, 4.33; N, 9.27. Found: C, 51.93; H, 4.39; N, 8.91.

EXAMPLE 29

5-Methoxy-1-(methyl)-4-[(4-methylthiophenyl)methyl]-3-(trifluoromethyl)pyrazole

The title compound was prepared as in Example 22 from the title compound in Example 28. The title compound, as an amber oil, was analytically pure as isolated from aqueous work-up.

Elemental analysis for: $C_{14}H_{15}F_3N_2OS$: Calc'd: C, 53.15; H, 4.78; N, 8.85. Found: C, 53.24; H, 5.05; N, 8.76.

The antihyperglycemic activity of the compounds of this invention was established by subjecting them to the following standard experimental procedure for that purpose:

Two to seven month old, male, db/db mice (35–60 g) are placed in seven groups of four (drug group) to six (vehicle group) mice. The test compound is administered in single oral doses, once a day, for four days. The control group receives vehicle only over the same period. Ciglitazone is employed as a positiv control, by gavage administration of 100 mg/kg/day. Food is supplied to the mice ad libitum during the test procedure. On the fourth day, blood plasma glucose levels are determined and compared with the vehicle group. The percent change in plasma glucose levels are determined at each dose to statistical significance of $p<0.05$.

The results of these tests are as follows:

TABLE

| Example | Dose (mg/kg) | % Change (Glucose) |
|---|---|---|
| 1 | 100 | −73 |
|   | 20 | −64 |
|   | 20 | −53 |
|   | 20 | −53 |
|   | 5 | −44 |
|   | 5 | −43 |
|   | 2 | −43 |
|   | 2 | −26 |
|   | 2 | −27 |
|   | 2 | −25 |
|   | 2 | −30 |
|   | 0.5 | −9 |
| 2 | 20 | −44 |
|   | 5 | −27 |
|   | 2 | −25 |
| 4 | 5 | −43 |
|   | 2 | −24 |

TABLE-continued

| Example | Dose (mg/kg) | % Change (Glucose) |
|---|---|---|
| 5 | 5 | −36 |
| 6 | 5 | −4 |
| 7 | 20 | −26 |
|   | 5 | −5 |
| 8 | 100 | −63 |
| 9 | 20 | −20 |
| 10 | 5 | −16 |
| 11 | 20 | −49 |
|   | 5 | −29 |
|   | 2 | −11 |
| 12 | 20 | −36 |
| 14 | 5 | −49 |
|   | 2 | −28 |
|   | 0.5 | −11 |
| 16 | 5 | −21 |
| 17 | 5 | −25 |
| 18 | 5 | −23 |
| 19 | 5 | −21 |
| 20 | 5 | −31 |
| 21 | 20 | −38 |
|   | 5 | −15 |
| 22 | 20 | −57 |
|   | 2 | −21 |
| 23 | 20 | −58 |
|   | 5 | −41 |
|   | 2 | −20 |
| 24 | 5 | −39 |
| 25 | 5 | −41 |
| 27 | 5 | −27 |
| 28 | 20 | −44 |
| 28 | 5 | −11 |
|   | 2 | −4 |
| 29 | 5 | −42 |
| Ciglitazone Standard | 100 | −33 |

From the experimental data obtained, it is apparent that the compounds of this invention reduce blood glucose levels, which characterizes them as antihyperglycemic agents useful in the treatment of disease states involving abnormally high blood levels of glucose, such as diabetes mellitus. As such, the compounds of this invention are to be administered to a mammal suffering from excessive blood levels of glucose in an amount from about 2 mg to about 100 mg per kilogram body weight, or more, per day, in single or multiple doses. An optimum dosing regimen to achieve the desired therapeutic response must be individualized for the patient by following the post-administration glucose blood levels. The dosage will vary with the compound administered and with the patient's age, weight, severity of disease state, response, etc., as is common in all therapeutic methods for control of glucose levels.

The compounds of this invention are orally active and may be made up in conventional unit dosage forms for administration. Compositions with inert diluents or edible carriers are compressed into tablets or filled in hard or soft gelatin capsules, with sufficient active ingredient to supply a daily dose or any fraction thereof. Slow release formulations are especially suitable for control of glucose with the compounds of this invention. Any suitable carrier known in the art can be used to prepare the pharmaceutical composition. In such a composition, the carrier is generally a solid or liquid or a mixture of a solid and a liquid.

Solid form compositions include powders, granules, tablets, capsules (e.g. hard and soft gelatine capsules), suppositories and pessaries. A solid carrier can be, for example, one or more substances which may also act as flavouring agents, lubricants, solubilisers, suspending agents, fillers, glidants, compression aids binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurized compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions from parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active, it can be administered orally either in liquid or solid composition form.

Preferably the pharmaceutical composition is in unit dosage form, e.g. as tablets or capsules. In such form the composition is sub-divided in unit dose containing appropriate quantities of the active ingredient; the unit dosage forms can be packaged compositions, for example packeted powders, vials, ampoules, prefilled syringes or sachets containing liquids. The unit form can be, for example, a capsule or tablet itself, or it can be the appropriate number dosage of any such compositions in package form. The quantity of the active ingredient in unit dose of composition may be varied or adjusted from about 2 mg or less to 100 mg or more, according to the particular need and the activity of the active ingredient. The invention also includes the compounds in the absence of the carrier where the compounds are in unit dosage form.

What is claimed is:

1. A process for treating hyperglycemia which comprises administering to a patient in need thereof, an antihyperglycemic amount of a compound of the formula:

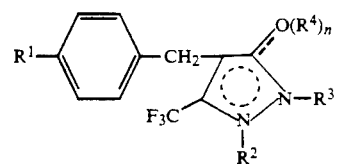

in which the dotted lines represent two sites of unsaturation appropriately located based on the identity of $R^2$, $R^3$ and $R^4$ and, $R^1$ is alkyl of 1 to 6 carbon atoms, perfluoroalkyl of 1 to 6 carbon atoms, alkoxy of 1 to 6 carbon atoms, perfluoroalkoxy of 1 to 6 carbon atoms, alkylthio of 1 to 6 carbon atoms, perfluoroalkylthio of 1 to 6 carbon atoms, alkylsulfinyl of 1 to 6 carbon atoms, alkylamino of 1 to 6 carbon atoms, halo, alkanoyl of 2 to 6 carbon atoms, 1-hydroxyalkyl of 1 to 6 carbon atoms or 1-(hydroxyimino) alkyl of 1 to 6 carbon atoms;

$R^2$ and $R^3$ are, independently, present or absent, and when present, $R^2$ is hydrogen or alkyl of 1 to 3 carbon atoms, and $R^3$ is hydrogen or alkyl of 1 to 3 carbon atoms;

$R^4$ is hydrogen or alkyl of 1 to 3 carbon atoms;

n is 0 or 1;

or a pharmaceutically acceptable salt thereof.

* * * * *